United States Patent [19]

Matsuura et al.

[11] Patent Number: 5,759,367
[45] Date of Patent: Jun. 2, 1998

[54] GAS SENSOR

[75] Inventors: Yoshinobu Matsuura; Toru Nomura; Daisuke Matsuda; Yuki Fujimori, all of Osaka; Maki Kitora, Hyogo, all of Japan

[73] Assignee: Figaro Engineering Inc., Osaka, Japan

[21] Appl. No.: 747,287

[22] Filed: Nov. 12, 1996

[30] Foreign Application Priority Data

Nov. 14, 1995 [JP] Japan .................. 7-321079

[51] Int. Cl.$^6$ .................. G01N 27/26
[52] U.S. Cl. .................. 204/424; 422/83; 422/98
[58] Field of Search .................. 204/424–429; 422/98, 83

[56] References Cited

U.S. PATENT DOCUMENTS 4,294,668  10/1981  Young .................. 204/424
5,228,975  7/1993  Yamada et al. .................. 422/98

FOREIGN PATENT DOCUMENTS 01313751A  12/1989  Japan .
6-347432   12/1994  Japan .

*Primary Examiner*—Bruce F. Bell
*Attorney, Agent, or Firm*—Nikaido, Marmelstein, Murray & Oram LLP

[57] ABSTRACT

An insulating glass film is formed on a heater film, and a gas sensitive film is formed on the glass film. The MgO content in the glass is kept at 0.1 wt % or under to prevent Mg from eluting into absorbed water at low temperatures and segregating on the cathode by the detection voltage.

7 Claims, 8 Drawing Sheets

FIG. 14 (1) Normal

FIG. 14 (2) Break Down (Strong)

FIG. 14 (3) Break Down (Weak)

FIG. 14 (4) Break Down (Un-Stable)

GAS SENSOR

FIELD OF THE INVENTION

The present invention relates to metal oxide semiconductor gas sensors and solid electrolyte gas sensors. In this specification gas is defined to include water vapour in addition to genuine gases such as CO, $H_2$, isobutane, propane, $CH_4$, $NO_x$, $O_2$ $O_3$ and $H_2S$.

PRIOR ART

The present applicant proposed a gas sensor comprising a substrate of alumina, etc. on which a heat-insulating glass film, a heater film, an insulating film, and a gas sensitive film are built up (Japanese Provisional Patent HE1-1-313751). The insulating film has a film thickness of, for example, about 10 μm, and is made of a glass or a mixture of glass and non-glass ceramic particle such as silica and alumina. When the substrate is a ceramic of low thermal conductivity, such as silica, there is no need of providing a heat-insulating glass film (Japanese Provisional Patent HE1-6-34732).

This gas sensor is suited to pulsatively heat a gas sensitive film, for example, a film of metal oxide semiconductor such as $SnO_2$ and a film of solid electrolyte such as proton conductor. The heat loss from the heater film to the substrate is reduced by the heat-insulating film, and the heater film and the gas sensitive film are built up with a thin insulating film in between to ease heat conduction between both the heater film and the gas sensitive film. When the heater film is pulsatively heated under these conditions, the gas sensitive film can be heated pulsatively, and in turn, the electric power consumption of the gas sensor can be reduced to, for example, 20~1 mW.

The present applicant found that the characteristics of such a gas sensor were unstable. Suppose, by way of explanation, the gas sensitive film is a metal oxide semiconductor film, and the detection target is CO. The applicant found that the resistance in CO increased with time and that the temperature characteristics of the metal oxide semiconductor changed with time. The applicant found, as a result of experiment, that the change of characteristics of the metal oxide semiconductor film proceeded rapidly in a high-temperature and high-humidity atmosphere, and that change was accelerated when a detection voltage was applied to the metal oxide semiconductor film during no pulse heating periods.

SUMMARY OF THE INVENTION

The task of the present invention is to reduce the variation of characteristics of a gas sensor comprising a substrate on which a heater film, an insulating film and a gas sensitive film are built up.

A secondary task of the present invention is to reliably prevent insulation breakdown between the heater film and the gas sensitive film.

The present invention is a gas sensor wherein a heater film, an insulating film having glass component, and a gas sensitive film are built up on a substrate, the Mg content of the glass composition of said insulating film on the gas sensitive side being kept, as converted to the MgO basis, at 2 wt % or under, preferably at 1.5 wt % or under, and most preferably at 0.1% or under. In the present specification, the Mg content is defined, as converted to the MgO basis, relative to the glass component, and the unit is wt % or wt ppm. The insulating film on the gas sensitive side is defined as the surface or a surface portion down to about 1 μm in depth therefrom of the insulating film on the gas sensitive film side.

One important thing in the present invention is to prevent contamination of the gas sensitive film by Mg. When the insulating film is composed of two layers, an upper layer on the gas sensitive film side and a lower layer on the heater film side, it is sufficient to reduce the Mg content of the upper layer, and there is no need of particularly limiting the Mg content of the lower layer. Besides the simple glass films described in the embodiments, a mixture of glass and non-glass ceramic particle such as silica, alumina and mullite may be used for the insulating film. In such a case, glass is present between ceramic particles and ceramic particles are coated by glass to become inert. Hence the Mg content in the ceramic particles is not particularly important, and as the greater part of the surface of the insulating film is covered by glass, it is sufficient to consider just the Mg content of the glass component.

Glass is available in various compositions, and it is hard to define the composition in a general manner. It is desired that glass contains SiO2, Al2O3 and RO so that its softening temperature is set in an easily handleable range of temperature from about 600° C. to about 1000° C. For example, pure silica glass has a high softening temperature, hence it is desired to lower the softening temperature of the pure silica glass by adding Al2O3 and RO to the glass. R is at least a member element of a group comprising Ca, Sr and Ba, and these elements are used as alkaline earth; Ca, Sr and Ba are simply called alkaline earth. The weight ratio of $SiO_2$, $Al_2O_3$ and RO may be, for example, 10~70:1~40:10~50 when the total weight of the three components is set at 100. In addition to these components, glass may contain transition metal oxide such as ZnO, $TiO_2$, $ZrO_2$. $TiO_2$ and $ZrO_2$ are substitution materials for $SiO_2$, and ZnO reduces, just like alkaline earth oxides, the softening point of glass. With regard to metallic elements, glass main contain lanthanoid such as La and Ce, and main group metallic elements such as Ga, In, Tl, Ge, Sn and Pb. Pb, however, is not desirable since Pb tends to diffuse easily in the gas sensitive film when glass is heated. In addition to them, B being a semimetal may be added; B may be added by, for example, 0 to 20 wt % as converted to $B_2O_3$. Furthermore, in addition to them, various elements such as halogen, As and Sb may be added to glass, thus the composition of glass may be varied. It is desired that glass has a low Mg content and its softening point is from 600° C. to 1000° C., and more preferably from 700° C. to 900° C. The mechanism of poisoning of the gas sensitive film by Mg is migration of Mg due to the electric field in the gas sensitive film. Alkaline metals are not desirable because they tend to migrate easily just like Mg. Be is not desirable because it is poisonous.

Preferred glass compositions are, for example, such that the total content of $SiO_2$, $Al_2O_3$ and RO is from 40 to 100 wt %, and the relative composition of $SiO_2$, $Al_2O_3$ and RO is, for example, from 10~70:1~40:10~50, the total of the three components being set at 100. The balance of the glass may be, for example, transition metal oxides at 0~30 wt %, lanthanoid oxides at 0~20 wt %, B2O3 at, for example, 0~20 wt %, and oxides of at least one member element of a group comprising Ga, In, Tl, Ge, Sn and Pb at 0~20 wt %. The residue is, for example, varied impurities such as halogen, As and Sb, and for example, is not more than 5 wt %. The Mg content of the glass composition on the gas sensitive film side is 2 wt % or under, preferably 1.5% or under, and most preferably 0.1 wt % or under. Preferably, the content of alkaline metal oxides is set at 0.5 wt % or under relative to the glass composition on the gas sensitive film side. Be is controlled to a trace, and PbO is set at 1 wt % or under, and preferably at 1000 wt ppm or under.

The insulating film is preferably composed of at least two layers, a lower layer on the heater film side and an upper layer of the gas sensitive film side, and at least for the upper layer, and preferably for both the upper layer and the lower layer, the Mg content in the glass composition is set, as converted to the MgO basis, at 2 wt % or under, preferably at 1.5 wt % or under, and most preferably at 1000 wt ppm or under.

The present inventor examined the mechanism of degradation with time of a pulse drive type gas sensor, and found that the degradation was caused by the migration of Mg ion from an insulating glass into a gas sensitive film. Let us assume, for the purpose of explanation, that the gas sensitive film is a metal oxide semiconductor. Degradation with time is small during a dry season (FIG. 6) and is large during a wet season (FIG. 7). Next, when the sensor is aged in a high-temperature and high-humidity atmosphere, the resistance of the sensor will increase rapidly after about 24 hours (Table 4). The degradation of the sensor is great when the detection voltage is applied to constantly, and is reduced when the detection voltage is made to synchronize with the heater pulse to shorten the time applying the detection voltage to (Table 4). The degradation of the sensor is most remarkable in a mode that the detection voltage is applied to constantly and heater pulse is not added to (Table 4).

When the gas sensitive film of a degraded sensor was put to element analysis, Mg ion was found to be segregated on the cathode. The Mg ion was diffused from the insulating glass into the gas sensitive film, and there were no other sources of the Mg ion. Zn ion was also detected as an impurity that was diffused from the insulating glass. The Zn ion in such a small quantity had no effects on the sensor characteristics. Hence the cause of the degradation was estimated to be the Mg ion which was diffused from the insulating glass into the gas sensing film. It was estimated as follows: When the sensor was cooled down near to the room temperature, the Mg ion was eluted from the insulating glass into adsorbed water, then the Mg ion was segregated by the detection voltage on the cathode to degrade the sensor characteristics. This corresponds to the fact that the degradation of the sensor is small during a dry season and the degradation is large during a wet season. It also corresponds to the fact that the degradation of the sensor proceeds significantly in a high-temperature and high-humidity atmosphere. Moreover, it also corresponds to the fact that the degradation is significant when the detection voltage is applied constantly and the degradation is decreased when the detection voltage is made to synchronized with the heater pulse. With regard to the mechanism of migration of the Mg ion, two mechanisms are possible: One mechanism is that the Mg ion that was eluted into adsorbed water near the room temperature is moved gradually by the detection voltage at low temperature, and the other mechanism is that the eluted Mg ion is moved rapidly upon pulse heating. The degree of degradation is more significant when pulse heating is not made, and from this it is certain that the degradation proceeds at low temperatures.

When all these findings are synthesized, we can expect that if the Mg content in the insulating glass is reduced, the degradation of the pulse drive type gas sensor can be prevented. An experiment (Table 6) showed results just as expected. It was also found that there were big differences in sensor characteristics between a glass with MgO content at 1 wt % and glasses with MgO content at 5 wt % and at 20 wt %, and that there were small differences in sensor characteristics between a glass with MgO content at 1 wt % and a glass with MgO content at 100 wt ppm. This indicates that MgO at about 1 wt % is stably present in the glass and will not be eluted out. Hence the MgO content is preferably kept at 2 wt % or under, more preferably kept at 1.5 wt % or under, and most preferably at 0.1 wt % or under. Moreover, the prevention of the degradation has a secondary effect of reducing the sensor resistance level and the dispersion thereof. Up to here the gas sensing film has been supposed to be a metal oxide semiconductor film. When the gas sensing film is, for example, a solid electrolyte film, eluted Mg ion will be moved by the electromotive force present in the solid electrolyte, and degradation similar to that of the metal oxide semiconductor film will proceed. In this case, the direction of the electric field in the gas sensing film is reverse, and the Mg ion will be segregated on the anode side rather than on the cathode side.

The present inventor found that when an insulating glass having no Mg ion was used, the insulation strength across the insulating glass and the heater film would decrease. This is attributed to that it is difficult to remove bubbles from a glass having no Mg ion and conductive channels of continuous air holes, etc. are formed in the insulating glass. It was found that when the insulating film was made in two layers, formation of continuous air holes penetrating through the insulating film would be reduced, improving the insulation strength thereof.

BRIEF DESCRIPTION OF THE DRAWINGS

FIG. 14(1)–14(4) are is a characteristic diagram showing output waveforms of gas sensors attendant on insulation breakdown.

EMBODIMENT

Figure 1:
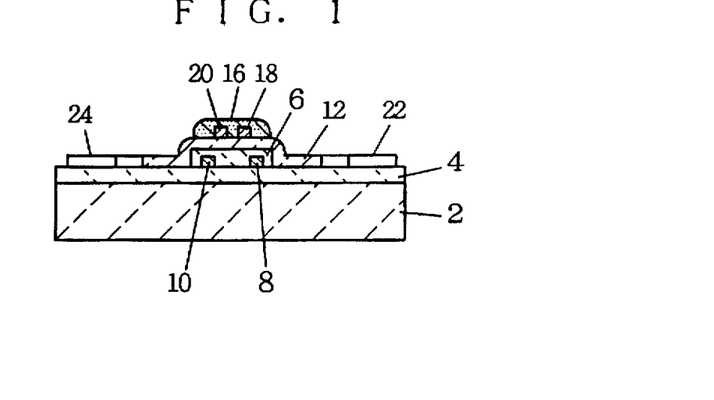
FIG. 1 is a sectional view of a gas sensor of an embodiment.
Figure 2:
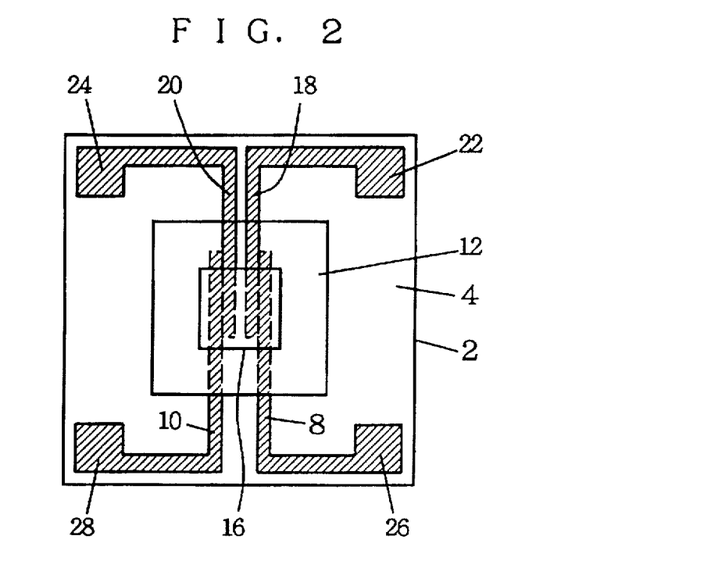
FIG. 2 is a plan view of the gas sensor of the embodiment.
Figure 3:
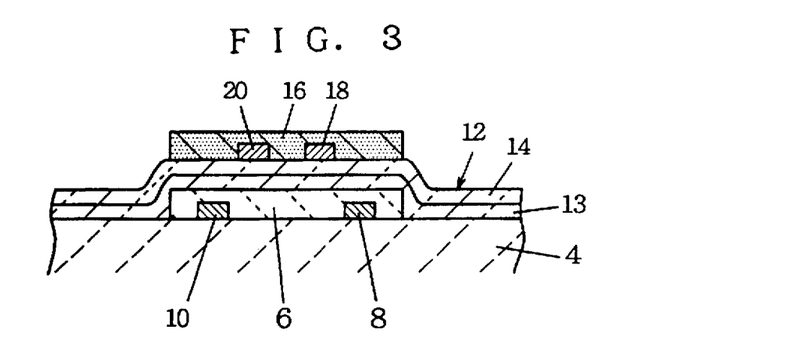
FIG. 3 is a fragmentary enlarged sectional view of the gas sensor of the embodiment.

An embodiment and related data are shown in FIG. 1 through FIG. 14. The structure of a gas sensor is shown in FIG. 1 through FIG. 3, and in these diagrams 2 denotes an insulating substrate of alumina, silica, mullite, etc. 4 is a insulating glass film for which silica glass, overcoat glass for hybrid integrated circuit, thermal head, etc., and the like are used. When the substrate 2 is a material of low thermal conductivity such as silica, the insulating glass 4 is not needed. 6 is a heater film for which $SuO_2$ film, Pt film, etc. are used, and it may be either a thin film or a thick film, and here an $RuO2$ film of about 10 μm in film thickness was used. 8 and 10 are heater films comprising Au films.

12 is an insulating film of which film thickness is, for example, from 5 to 20 μm, and preferably it is composed of two layers, a lower layer 13 and an upper layer 14, as shown in FIG. 3. This is intended to increase the insulation strength across the heater film 6 and the gas sensitive film 16: With the use of two layers, continuous air holes penetrating from the heater film 6 to the gas sensitive film 16 are eliminated to increase the insulating strength. The insulating film 12, both the upper layer 14 and the lower layer 13, was made of glass, but non-glass ceramic particles such as silica, alumina, mullite, etc. may be mixed with glass to form a layer of mixture of glass and ceramic. The glass content of the insulating layer 12 is preferably from 20 to 100 wt %. In preventing contamination of the gas sensitive film 16 by Mg, what is important is to set the Mg content of the glass component of the upper layer 14, as converted to the MgO basis, at 2 wt % or under, preferably at 1.5 wt % or under, and most preferably at 1000 wt ppm or under. Regarding the lower layer 13, the Mg content (in the following, the content in glass will be expressed as converted on the MgO basis, and the contents of other components will also be expressed in a similar method) may exceed 2 wt %, but preferably, one same material is used for both the lower layer 13 and the upper layer 14, and the MgO content is set at 2 wt % or under, more preferably at 1 wt % or under, and most preferably at 1000 wt ppm or under.

Regarding the insulating film 12, it is desirable to set the MgO content of the upper layer 14 at 2 wt % or under, and in addition to it, it is preferable to use glass of which softening point is from 600° to 1000° C., and it is more preferable to use glass of which softening point is from 700° to 900° C., and moreover, it is desirable to prevent damages to the heater film 6 and the Au heater films 8, 10 during film formation. It is desirable that the lower limit of the softening point is fairly higher than the highest heating temperature of the heater film 6 (300°~450° C.), hence the lower limit is set at 600° C. or over, and more preferably at 700° C. or over. As restraints are given to the range of the softening point, restraints will be generated to glass composition that may be used for the insulating film 12. For instance, the softening point of silica glass is about 1500° C., and the softening point can be reduced to around 1200° C. by adding an impurity or impurities, but silica glass is used only for gas sensors of high temperature service. This is not to exclude, in anyway, silica glass. As the softening point must be set within an appropriate range, glass composition is limited to those of which main components are $SiO2$, $Al2O3$ and RO (R is at least a member of a group comprising Ca, Sr and Ba, and hereinafter this may be called alkaline earth). Commercial glasses of $SiO_2$—$Al_2O_3$—RO system of which softening point is from 700° to 900° C. have weight ratios of 10~70:1~40:10~50 when the total weight of the three components is set at 100. In the embodiment, Ca and Ba were used as alkaline earth, and neither Ca nor Ba did not contaminate the gas sensitive film nor affect the characteristics of the gas sensitive film. Hence it is clear that Sr having a property intermediate between Ca and Ba can be used.

A wide variety of compositions are known for commercial glasses, and to $SiO_2$—$Al_2O_3$—RO glasses of which softening point is from 700° to 900° C., transition metal oxides such as ZnO, $ZrO_2$ and $TiO_2$ may be added. ZnO plays a role similar to that of RO, and the addition is, for example, from 0 to 25 wt %. The present inventor found that ZnO partly migrated from the upper layer 14 into the gas sensitive film 16 to contaminate the gas sensitive film 16. However, it was also found that ZnO being an impurity did not affect the characteristics of the gas sensitive film 16. Thus ZnO will contaminate the gas sensitive film 16 but will not affect the characteristics. $ZrO_2$ and $TiO_2$, etc. are components that substitute $SiO2$, and the addition is, for example, from 0 to 15 wt %. In addition to them, it is conventional to add Mn, Fe, Cu, etc. to glass, and these transition metals may be added to glass. The content of transition metals in glass is preferably from 0 to 30 wt % as converted to their oxides. It is well known that $B2O3$ is added to glass as a substitution product of $Al2O3$. $B2O3$ can be easily corroded by alkali. The present inventor, however, confirmed by another experiment (details are omitted here) that $B_2O_3$ in the insulating film 12 did not affect the characteristics of the gas sensitive film 16. A glass having 30 wt % of $B_2O_3$ was used for an insulating film 12, and the insulating film 12 was made to corrode in an NH3-containing atmosphere till the surface became rugged. Even under this condition, the characteristics of the gas sensitive film 16 did not change. To control corrosion of the insulating film 12, it is desirable to keep the $B_2O_3$ content in a range from 0 to 20 wt %. It is well known to add main group metallic elements such as Ge and Sn to glass. For example, there is no problem for a gas sensitive film comprising $SnO2$ to include Sn as an impurity. The main group metallic elements that are normally used include Ga, In, Sn, Ge, Tl and Pb, and their addition is, as converted to the oxide basis, from 0 to 20 wt %. Of these elements, Pb was found, in a different experiment, to contaminate the gas sensitive film 16 when the gas sensitive film 16 was heated in the film formation process. Hence the Pb content is set at 1 wt % or under as converted to the PbO basis, and preferably at 1000 wt ppm or under.

In addition to those mentioned above, it is known to add lanthanoid such as La and Ce to commercial glasses, and they are mainly substitution products of $Al_2O_3$. The addition of lanthanoid is preferably from 0 to 20 wt % as converted to the trivalent oxide basis. Moreover, various impurities such as halogen, As and Sb may be added to glass, and their total content is preferably 5 wt % or under when halogen is converted to the simple substance basis and As and Sb are converted to the trivalent oxide basis. In another experiment, alkaline metals such as Na were found to contaminate the gas sensitive film 16. Hence the content of alkaline metals is set at 0.5 wt % or under, as converted to the oxide basis, and more preferably at 0.1 wt % or under. Be must be kept to a trace.

When all the requirements mentioned above are combined together, a preferable glass composition for the upper layer 14 will be as follows, and the same composition is also preferable for the lower layer 13:

$$(SiO_2\text{a-}Al_2O_3\text{b-ROc})1\text{-d-} \quad M1Oe\text{-}M2Of\text{-}Ln_2O_3g\text{-}B_2O_3h\text{-}Xi.$$

where M1 is transition metal oxide, M2 is main group metal oxide, and $Ln2O3$ is lanthanoid oxide.

X is an impurity other than those mentioned above, and MgO content is 2 wt % or under, and preferably 1.5 wt %, and most preferably 0.1 wt % or under, and the alkaline metal oxide content is preferably 0.5 wt % or under, and more preferably 0.1 wt % or under, and the PbO content is preferably 1 wt % or under, and more preferably 0.1 wt % or under, and BeO is kept to a trace, and when a through i are weight ratio units and the total of the composition is set at 100, a is 10~70, b is 1~40, c is 10~50, d is 0~0.5 and e is 0~30 and more preferably 0~20, f is 0~20 and more preferably 0~10, g is 0~20 and more preferably 0~10, h is 0~20 and more preferably 0~10, and e is 0~5.

16 is a gas sensitive film made of a metal oxide semiconductor film such as $SnO_2$, $In_2O_3$, $WO_3$ and ZnO or a solid electrolyte such as proton conductor, and may be either a thin film or a thick film, and in the embodiment, an SnO2 film of 10 μm thick was used. 18 and 20 are detection electrodes using Au film, and even numbers 22 through 28 are electrode pads.

Drive Circuit

Figure 4:
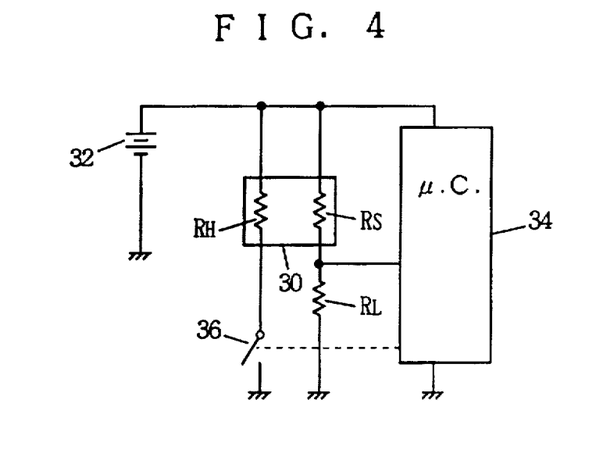
FIG. 4 is a diagram showing a drive circuit of the gas sensor of the embodiment.
Figure 5:
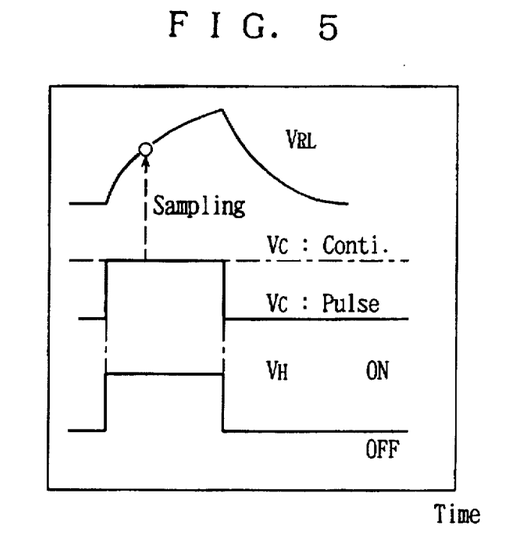
FIG. 5 is a characteristic diagram showing an operating waveform of the gas sensor of the embodiment.

A drive circuit of the gas sensor is shown in FIG. 4 and FIG. 5. In FIG. 4, 30 denotes a gas sensor, Rs denotes the resistance of a gas sensitive film 16, and RH denotes the resistance of a heater film 6. RH was about 30Ω at room temperature and about 20Ω at the highest heating temperature. The temperature of the gas sensitive film 16 was measured from the resistance of a thermistor film provided in place of the gas sensitive film 16. 32 is a power source of, for example, 5 V. 34 is a micro controller, and 36 is a switch for pulse-driving the heater film 6. RL is a load resistance.

The gas sensor 30 is driven as shown in FIG. 5. For example, the switch is turned on for 8~16 milliseconds in every one second, and the detection voltage (for example, 5 V) is applied in synchronization with the heater pulse or is constantly applied. Preferably, the detection voltage is made to synchronize with the pulse so that it is applied pulsatively for a time width just sufficient to measure the sensor output VRL (output to the lord resistance RL). Hence the pulse width of the detection voltage may be shorter than the width of the heater pulse. When a heater pulse is applied, the output VRL will change as shown in the top of FIG. 5. Sampling is made with an appropriate timing (in the embodiment, about 2 milliseconds after the application of heater impulse). The highest heating temperature of the gas sensitive film 16 is about 300° C. when the heater pulse width is 8 milliseconds, and about 450° C. when the pulse width is 16 milliseconds.

Test Cases

Glasses of the following compositions were used to prepare gas sensors of the embodiments 1 through 3 and gas sensors of the controls 1 and 2.

The sensors of embodiments 1 and 2 were equivalent to each other in characteristics, and the sensors of controls 1 and 2 were equivalent to each other in characteristics. Hence in the following the explanation will be given by comparing the sensor of embodiment 1 and the sensor of control 1 with each other. The data of FIG. 6 through FIG. 9 were measured by producing the sensors of the control prior to the development of the embodiment. The driving conditions of the sensor 30 are, if not specified otherwise, that the detection voltage VC (5 V) is applied constantly, and a heater pulse (5 V) is applied for 8 milliseconds in every 1 second. Under these conditions the sensor 30 is driven constantly.

TABLE 1

| Composition | Glass compositions | | | | |
| --- | --- | --- | --- | --- | --- |
| | Embodiment 1 | Embodiment 2 | Embodiment 3 | Control 1 | Control 2 |
| SiO2 | 40 | 60 | 50 | 45 | 43 |
| Al2O3 | 5 | 2 | 4 | 4 | 15 |

TABLE 1-continued

| CaO | 1 | 15 | 20 | 10 | 10 |
| --- | --- | --- | --- | --- | --- |
| BaO | 35 | 18 | Trace | 4 | 15 |
| SrO | Trace | Trace | Trace | Trace | Trace |
| ZnO | 15 | 1 | 20 | 20 | 10 |
| B2O3 | Trace | Trace | 3 | Trace | Trace |
| TiO2 | Trace | Trace | Trace | Trace | Trace |
| Ce2O3 | 2 | 2 | Trace | Trace | Trace |
| Halogen | Trace | Trace | Trace | Trace | Trace |
| MgO | 0.01 | 0.01 | 1 | 15 | 5 |
| Alkali metal | 0.05 | 0.05 | 0.2 | 0.05 | 0.05 |
| Pb | 0.02 | 0.02 | 0.03 | 0.02 | 0.02 |
| Trace imurities and MgO in total | 2 | 2 | 3 | 17 | 7 |

\* The unit of composition is weight %. The insulating film 12 is one layer of 10 μm in film thickness. The greater part of alkaline metals is Na and K. The greater part of halogen is Cl and Br. Components other than halogen are indicated as converted to the oxide basis. The baking temperature of the insulating film is 750° C. For each glass, when various trace impurities and MgO, alkaline metal oxides, halogen and PbO are added to the components each accounting for 1 wt % or over, the total will be 100%.
\* The SnO2 film (1 wt % of Pt was added) was formed in a film of 10 μm thick, then it was baked at 600° C.

Figure 6:
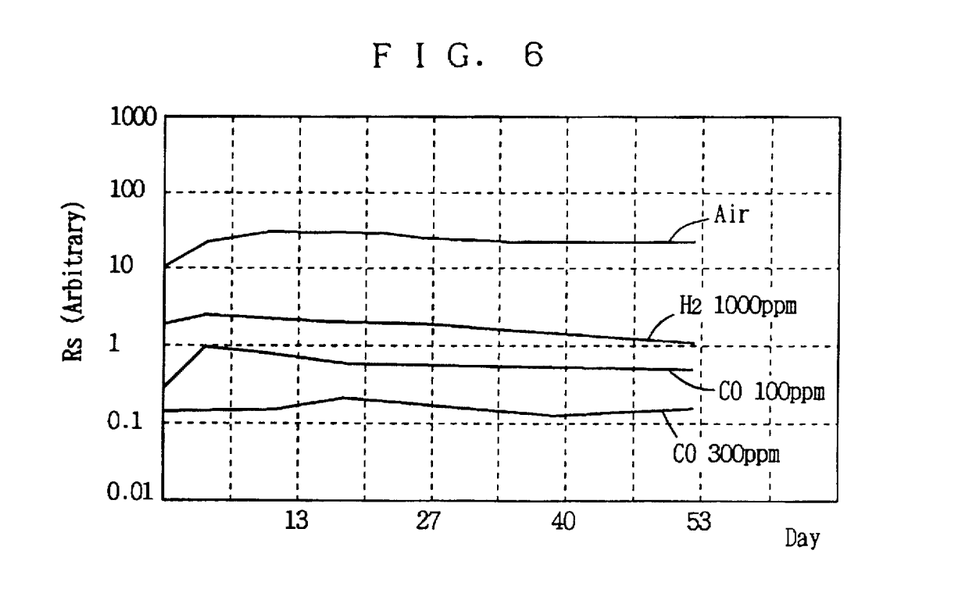
FIG. 6 is a characteristic diagram showing resistance drifts of a conventional gas sensor in a dry season.
Figure 7:
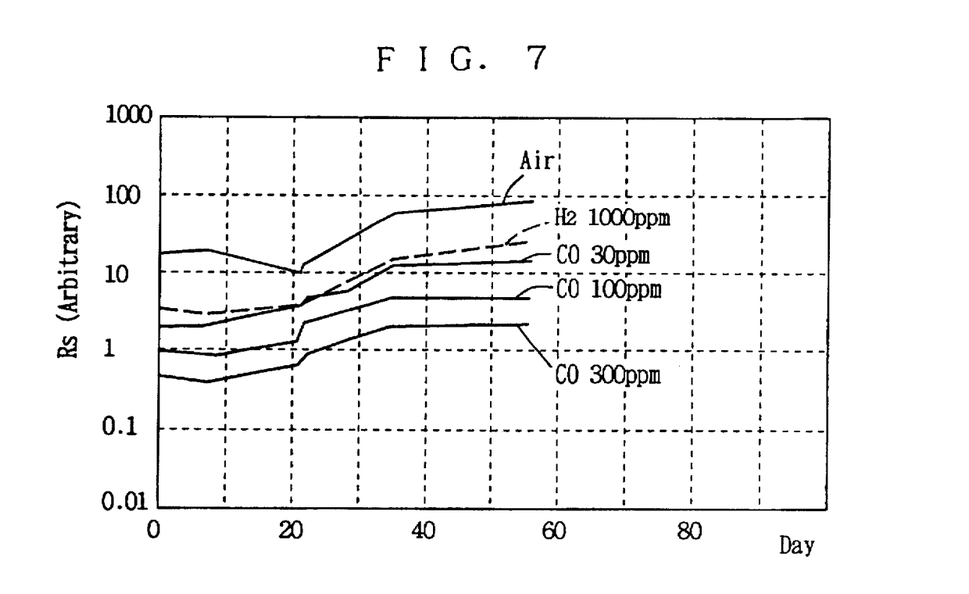
FIG. 7 is a characteristic diagram showing resistance drifts of a conventional gas sensor in a wet season.
Figure 8:
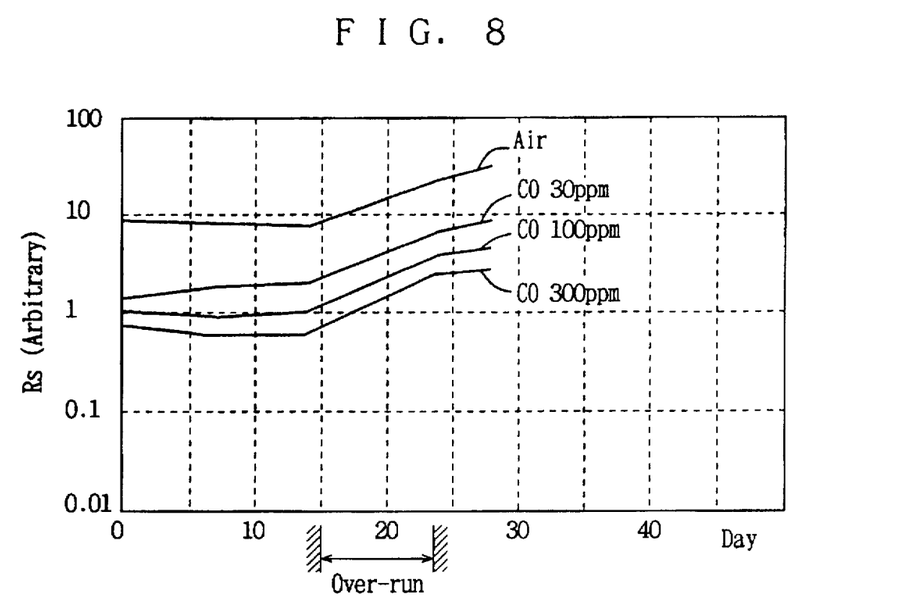
FIG. 8 is a characteristic diagram showing resistance drifts of a conventional gas sensor upon overrun of the control circuit.
Figure 9:
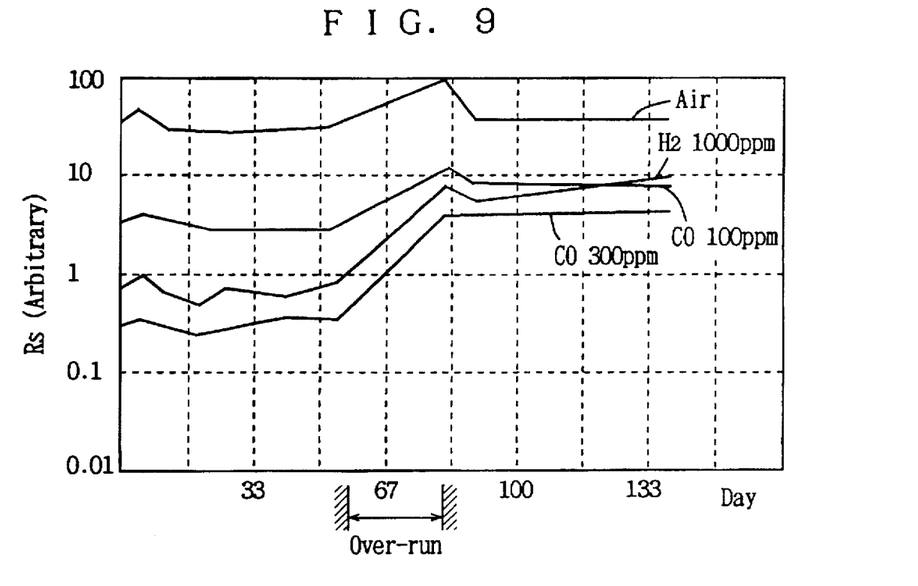
FIG. 9 is a characteristic diagram showing resistance drifts of a conventional gas sensor upon overrun of the control circuit.

FIG. 6 shows the characteristics of the sensors of control 1 measured over seven weeks starting from Feb. 13, 1995. The number of the sensors tested was thirteen. The diagram shows the average characteristics over a period in a dry season. FIG. 7 shows the characteristics of the sensors of control 1 measured over eight weeks starting from Jun. 12, 1995. The number of the sensors tested was ten. When the wet season (FIG. 7) and the dry season (FIG. 6) are compared with each other, changes in the characteristics with time were more significant in the wet season. Generally speaking, as a result of changes in characteristics with time, the resistances of the sensors will become higher. FIG. 8 and FIG. 9 show cases where the sensor resistances increased significantly in only one to four weeks. The resistances increased by a factor of 3 (FIG. 8, the number of sensors is 6) and by a factor of a little short of 10 (FIG. 9, the number of sensors is 5). As the phenomena shown in FIG. 8 and FIG. 9 were discovered, the energizing systems of the sensors were examined. As a result, traces of overrun of the micro controllers for control 34 were found for the periods indicated in the diagrams. The particulars of overruns were estimated that due to the structure of the microcontroller, the heater pulse VH was turned off and the detection voltage VC were constantly applied. The period of the occurrence of overrun was around July 1995 for FIG. 8, and around April 1995 for FIG. 9. From these findings, it was found that the changes with time of the sensors were significant in a wet season and proceeded rapidly when no heater pulse was applied.

Figure 10:
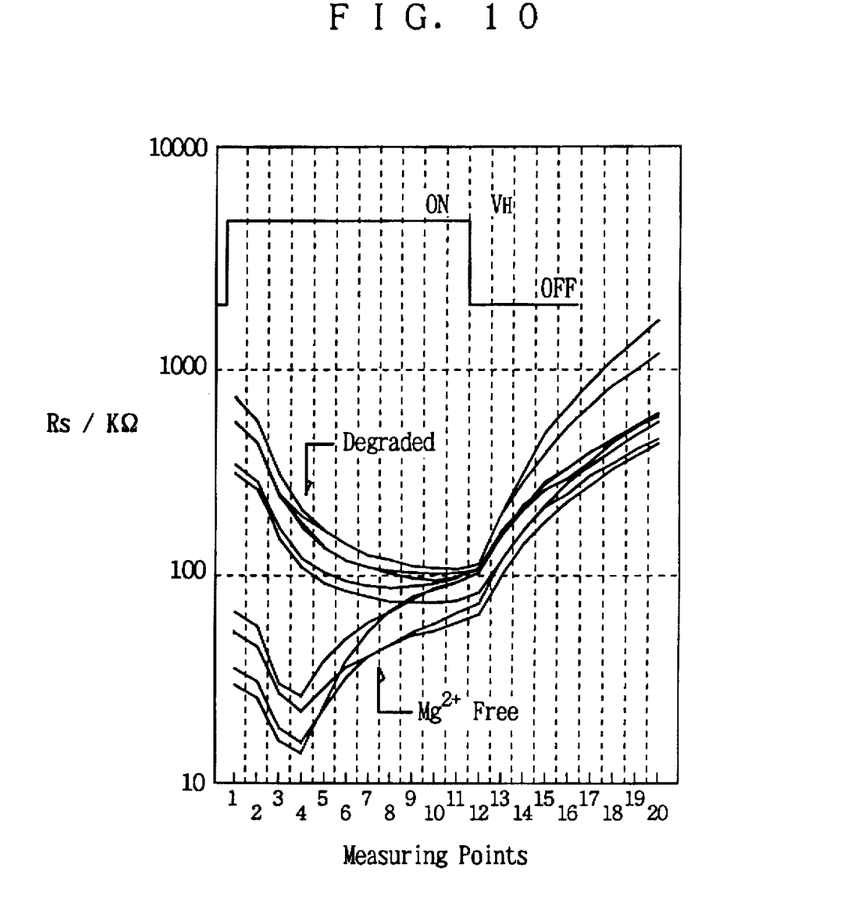
FIG. 10 is a characteristic diagram showing changes in the resistance in 100 ppm of CO with the advancement of diffusion of Mg ion into a gas sensitive film.

FIG. 10 shows sensor resistances of the sensors that experienced abnormally high resistances (phenomena of FIG. 8 and FIG. 9) (controls 1 and 2) and of the sensors of the embodiment 1 upon application of heater pulse. The atmosphere was 100 ppm of CO, and twelve points 1 through 12 were sampled while the heater pulse was on for 8 milliseconds (the waveform is indicated in the top portion of the diagram). The temperature characteristics of the sensor of embodiment 2 were similar to those of the sensor of embodiment 1. The difference between embodiment 1 and embodiment 2 was a difference between their respective Zn contents. However, no effects on the sensor characteristics were detected. The sensors that showed abnormally high resistances and the sensors of embodiment 1 were different in temperature characteristics, and the results were clearly divided into two groups. When the sensors experienced the abnormally high resistance phenomenon, the minimum value of the sensor resistance around the point 4 disappeared. In the sensors of controls 1 and 2, dips of resistance appeared around the point 4 in CO immediately after the production.

Figure 11:
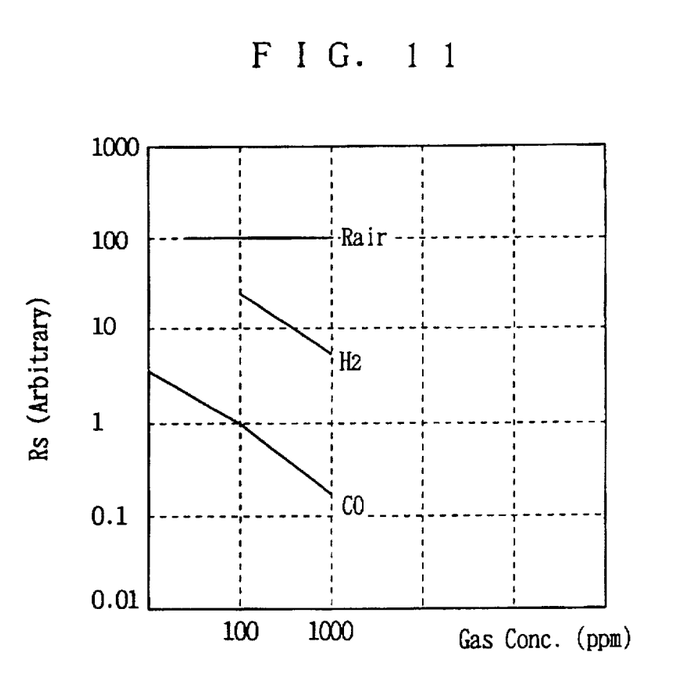
FIG. 11 is a characteristic diagram showing gas concentration characteristics after contamination of a conventional gas sensor by Mg.
Figure 12:
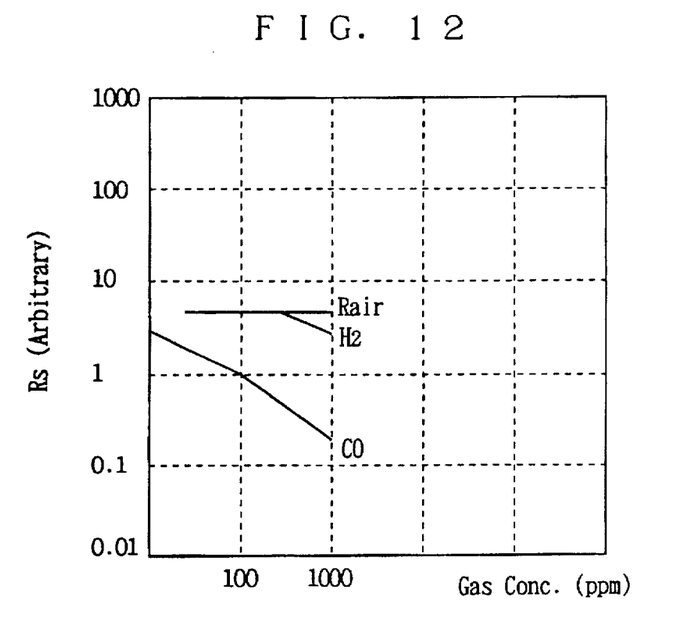
FIG. 12 is a characteristic diagram showing gas concentration characteristics of the gas sensor of the embodiment.

FIG. 11 shows the characteristics of the sensors of control 1 (the number of the sensors was 15). The heater pulse had a width of 9 milliseconds, and the characteristics two milliseconds after the start of pulse heating were measured. The sensors were energized for about one week after production, and did not experience the abnormally high resistance phenomenon. FIG. 12 shows the characteristics of the sensors of embodiment 1 (the number of the sensors was 15), and the measuring conditions were similar to those of FIG. 11. The characteristics were those about one week after the start of energization. The average resistance in 100 ppm of CO was 18.4 k Ω for FIG. 11, and 2.5 k Ω for FIG. 12. When an insulating glass 12 containing MgO was used, the sensor resistance increased and the sensitivity to H2 also increased.

The sensors of control 1, both those that experienced the abnormally high resistance phenomenon (defective units) and those that did not experience the phenomenon (non-defective units), were examined. Their gas sensitive films 16 were subjected to X-ray local analysis; elemental analysis was made by wavelength dispersion spectroscopy (WDS). Impurities other than the naturally present elements such as Sn and Pt were Mg and Zn, and no mixing of Ca and Ba was detected. All detected Mg and Zn were found to have migrated from the insulating glass 12. The analytical results of the regions between the detection electrodes 18 and 20 are shown in Table 2. There were no significant difference between the defective units and the non-defective units. Next, the gas sensitive films around the detection electrodes 18 and 20 were subjected to elemental analysis. The results concerning Mg ion distribution are shown in Table 3. Zn ion distributed evenly and no segregation was found. Hence the indication of the results is omitted.

TABLE 2

Elemental Analysis of Inter-electrode Area

| Element | Non-defective unit | Defective unit |
|---------|--------------------|----------------|
| Sn | 18200 | 17500 |
| Mg | 230 | 180 |
| Zn | 250 | 200 |

* The results are shown in count.

TABLE 3

Mg Distribution Around Electrodes

| Sensor | Anode | Cathode |
|--------|-------|---------|
| New product | 132 | 130 |
| Energized, without abnormally high resistance phenomenon | 98 | 181 |
| Abnormally high resistance phenomenon | 85 | 250 |
| Abnormally high resistance phenomenon | 188 | 246 |

* The results are shown in count.

As clearly seen in Table 2 and Table 3, Mg has been diffused in the gas sensitive film 16 even in sensors immediately after the production. As degradation proceeds, Mg will segregate on the cathode side. According to the results of Table 2, even though the phenomenon of abnormally high resistance occurred, the Mg concentration did not increase in the inter-electrode area. It was the segregation of Mg to the cathode that showed a close correlation with the phenomenon of abnormally high resistance. FIG. 8 and FIG. 9 indicate that the degradation of sensors proceeded when no heater pulse was applied. FIG. 6 and FIG. 7 show that the degradation proceeded significantly in a wet season. Then two conditions were prepared: One was to synchronize the detection voltage with the heater pulse, and to apply both the voltage and the pulse for the same period and at the same time (VC synchronization). The other one was to apply VC constantly. Then the sensors were aged in a high-temperature and high-humidity atmosphere. Table 4 shows the average sensor resistance (the number of the sensors was 7) measured in an atmosphere of 100 ppm of CO after aging.

TABLE 4

Effects of VC and VH

| Sensor resistance (Ω) | Initial value | After test |
|-----------------------|---------------|------------|
| Aging conditions: 50° C. × relative humidity of 100%, 24 hours. | | |
| Pulse width 9 milliseconds | | |
| VC constant | 27 | 290 |
| VC synchronized | 19 | 17 |
| Pulse width 16 milliseconds | | |
| VC constant | 42 | 1400 |
| VC synchronized | 48 | 42 |
| Aging conditions: 60° C. × relative humidity of 90%, 1 hour. | | |
| Pulse width 9 milliseconds | | |
| VC constant | 32 | 34 |
| VC constant and VH off | 27 | 175 |

When VC was applied constantly, the degradation was significant. In particular, when VC was applied constantly and VH was turned off, the degradation proceeded extremely. In this mode, the resistance increased about six times in 1 hour of aging. The degrading mechanism of the sensor 30 estimated from these findings is that the Mg component in the insulating glass 12 is diffused in the gas sensitive film 16 and migrated by the detection voltage to segregate on the cathode side. As the degradation was significant when VH was off, it is estimated that the degradation proceeded at low temperatures and the Mg ion was eluted into adsorbed water, etc. and moved by the detection voltage. The state of segregation of Mg ion of the sensors of control 1, after one hour of aging under the conditions of 50° C.×relative humidity of 100% (VC was applied continuously, and VH was off) shown in Table 5. The Mg concentration increased due to aging, and in particular, the Mg concentration increased significantly on the cathode side. This agrees well with the above-mentioned mechanism of degrading and shows that thermal degradation attendant to the application of heater pulse is small. In other words, it is conceivable that pulse heating may make adsorbed water boil rapidly, and attendant to this boiling corrosion of the insulating film 12 may proceed. This, however, does not agree with the data obtained. Hence the mechanism of degradation is the elution of Mg into adsorbed water at low temperatures and the segregation of Mg to the cathode by the detection voltage.

TABLE 5

| | Distribution of Mg | | | |
|---|---|---|---|---|
| | Before test | | After test | |
| Sensor lot | Anode | Cathode | Anode | Cathode |
| 1 | 136 | 135 | 182 | 227 |
| 2 | 90 | 87 | 150 | 228 |
| 3 | 85 | 90 | 113 | 162 |

* The results show Mg accounts. 1 through 3 are different production lots.
* 50° C. × relative humidity of 100% × 1 hour. VC is constant. VH is off.

Figure 13:
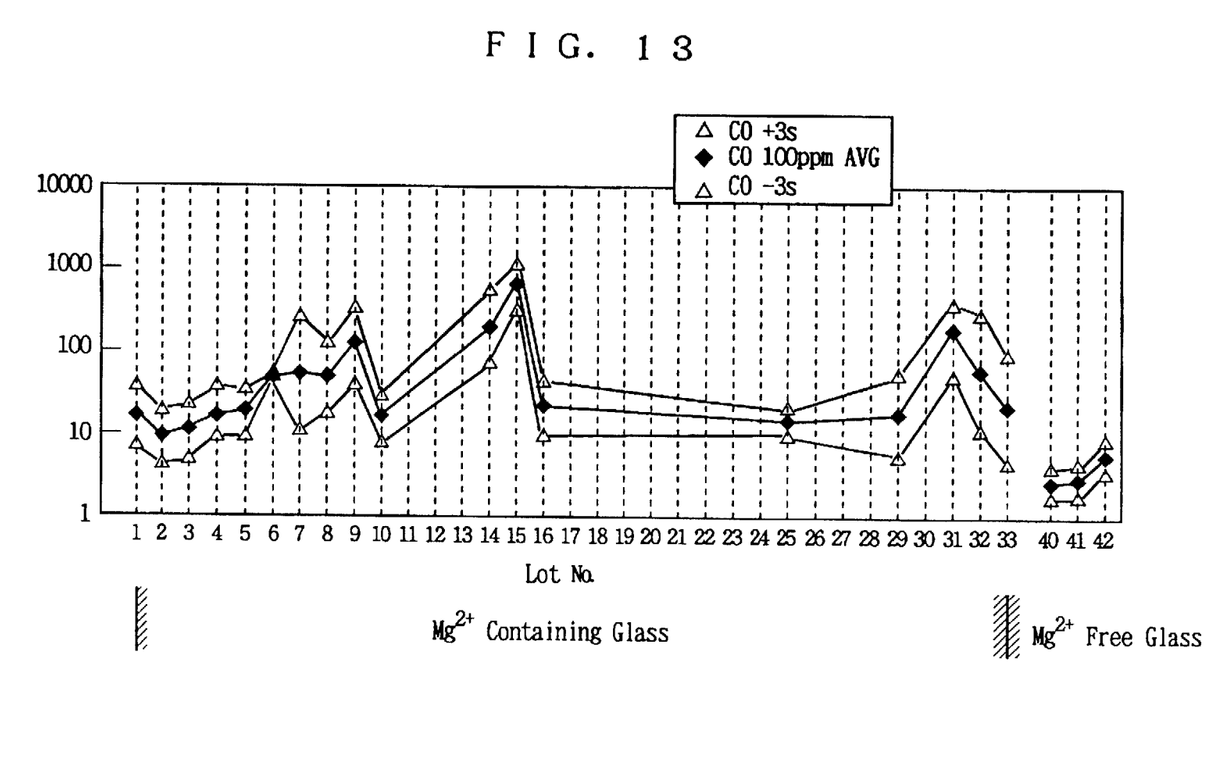
FIG. 13 is a characteristic diagram showing changes in the resistances of the gas sensors by lot.

The sensors of embodiments 1 through 3 and the sensors of controls 1 and 2 were aged in an atmosphere of 50° C. and relative humidity of 100% for 24 hours, and during this period VH was applied as pulses (9 millisecond/second) and VC was applied constantly. The resistances in an atmosphere of 100 ppm of CO after the test (at the third point of FIG. 10, unit is k Ω) are shown in Table 6. Embodiment 1 contains 20 wt % of ZnO in its glass but it had no effects on the sensor characteristics. Embodiment 3 having 1 wt % of MgO shows characteristics similar to those of embodiment 1 and embodiment 2. As is clear from Table 6, glass containing 1 wt % of MgO is practicable, hence the upper limit of the MgO content is set at 2 wt %, and more preferably at 1.5 wt %, and most preferably at 0.1 wt %. Moreover, even if a glass of which MgO content is close to 2 wt % causes degradation of a sensor, the degradation can be controlled by synchronizing VC with VH as shown in Table 4. Eliminating MgO from the insulating glass 12, and in particular from the upper layer 14 thereof, will lower the sensor resistance, easing its handling, and significantly improve the durability. The present inventor had been thinking that the durability of this kind of sensor was determined by the driving method itself, the pulse drive system. However, the durability was improved dramatically by eliminating the diffusion of impurities from the insulating glass. For the Mg-containing glass (control 1) and the Mg-free glass (embodiment 1), changes in resistance and range of resistance distribution (the range of ±1S; S is the standard deviation) are shown in FIG. 13. With the use of glass containing no Mg, the dispersion of resistances is reduced.

TABLE 6

| 50° C. × 100%, 24 hours Test | | |
|---|---|---|
| | Before test | After test |
| Control 1 | 22 | 420 |
| Control 2 | 25 | 370 |
| Embodiment 1 | 2.34 | 2.27 |
| Embodiment 2 | 2.42 | 2.51 |
| Embodiment 3 | 3.51 | 4.84 |

* The number of sensors is three for each group, and the results are resistances in average in an atmosphere of 100 ppm of CO (the sampling point is the third one). VH is pulse, and VC is continuous.

Insulation Strength

Figure 14:
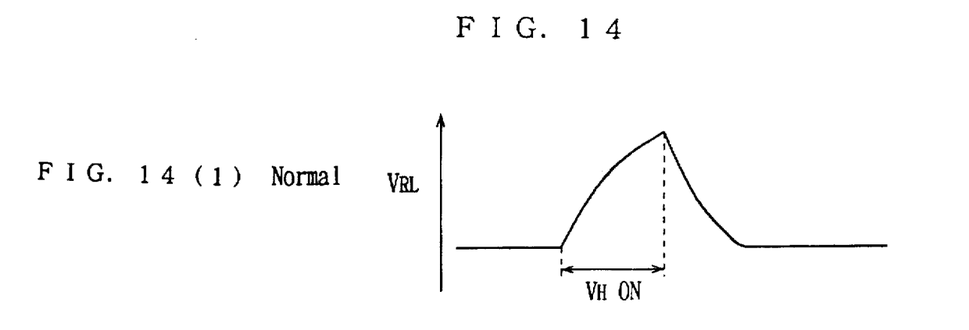

FIG. 14 shows the waveforms of sensor outputs attendant to the application of the heater pulse. The present inventor used oscillograph and confirmed the waveforms of 1) through 4) of FIG. 14. 1) is a normal waveform. 2) shows a strong insulation breakdown. In the drive circuit of FIG. 4, due to the strong insulation breakdown, the detected current escaped to the switch 36, and the detection output decreased in synchronization with the heater pulse. 3) shows a weak insulation breakdown. When the switch 36 was turned on, a part of the detected current escaped to the switch 36 and the output decreased. When the switch 36 was turned off, the leakage to the switch 36 was stopped, and the output increased. 4) shows an unstable insulation breakdown. It indicates spike discharges. The frequencies of insulation breakdown are greater in embodiments 1 and 2 than in controls 1 and 2. This indicates that it is more difficult to eliminate bubbles from Mg-free glass during the formation of films. Organic solvent and residue of binder used in the glass film formation and air bubbles caught between the glass film and the heater film 6 are slow to escape. It is estimated that they produce continuous air holes in the insulating film 12 to cause insulation breakdown.

The present inventor found that forming the insulating glass 12 in two layers, an upper layer 14 and a lower layer 13, was able to eliminate continuous air holes, and in turn, to prevent insulation breakdown. The present inventor also found that the preferred film thickness of the insulating glass 12 was 20 μm or under, and that when the film thickness was increased above 20 μm the highest heating temperature of the gas sensitive film during pulse driving would be lowered. The results are shown in Table 7. It is evident that when the insulating film 12 is made in two layers a total film thickness of 5 μm and over can prevent insulation breakdown. In case of a single layer, with a film thickness around 5 μm, the insulation breakdown frequency still remains around 20%. In the case of two layers, it is also evident that it is sufficient to control the Mg content of the upper layer 14. In the embodiments, SnO2 film was used for the gas sensitive films. However, it is also evident that other films may be used. When a solid electrolyte film is used, no detection voltage will be applied externally. However, similar segregation of Mg will be generated by an electromotive force of the solid electrolyte itself. Hence the present invention is also applicable to other gas sensitive films as well as those of metal oxide semiconductor films.

TABLE 7

| Insulation Breakdown Frequency/400 units | | |
|---|---|---|
| Total film thickness (μm) | Number of layers | Breakdown frequency/ 400 units |
| 4.6 | 1 | 82 |
| 3.3 | 2 | 26 |
| 5.1 | 2 | 0 |
| 7.9 | 2 | 0 |

* The insulation breakdown cases include the respective waveforms of 2) through 4) of FIG. 14, including unstable breakdowns. The upper and lower layers of the two layer formation have substantially identical film thicknesses.

We claim:

1. A gas sensor, comprising a heater film, an insulating film having a gas sensitive side and a heater film side wherein said insulating film contains a glass component, and a gas sensitive film, wherein a Mg content of the glass component in said insulating film on the gas sensitive side is kept, as converted to the MgO basis, at 2 wt % or under.

2. A gas sensor of claim 1 wherein said glass component includes at least $SiO_2$, $Al_2O_3$ and RO, wherein R denotes at least one member of a group consisting of Ca, Sr and Ba, and wherein the Mg content in the glass component on the gas sensitive side is kept, as converted to the MgO basis, at 2 wt % or under.

3. A gas sensor of claim 2 wherein the total content of $SiO_2$, $Al_2O_3$ and RO of said glass component is from 40 to 100 wt %, and wherein the balance of the glass component consists of at least a member element of a group comprising transition metals, lanthanides, B, Ga, In, Tl, Ge, Sn and Pb, at least a member element of a group comprising oxygen and halogen, and impurities of 5 wt % or under, and wherein the MgO content of the glass component of the insulating film on the gas sensitive film side is kept at 1000 wt ppm or under.

4. A gas sensor of claim 1 wherein said insulating film consists of at least two layers, a lower layer on the heater film side and an upper layer on the gas sensitive film side and wherein the Mg contents of the glass components of both the lower layer and the upper layer are kept, as converted to the MgO basis, at 2 wt % or under.

5. A gas sensor of claim 1 wherein said insulating film consists of at least two layers, a lower layer on the heater film side and an upper layer on the gas sensitive film side and wherein the Mg content of the glass component of the upper layer is kept, as converted to the MgO basis, at 2 wt % or under.

6. A gas sensor as in claim 1, wherein said heater film, insulating film and gas sensitive film are built up on a substrate.

7. A gas sensor, comprising a heater film, an insulating film having a gas sensitive side and a heater film side wherein said insulating film contains a glass component, and a gas sensitive film, wherein a Mg content of the glass component in said insulating film on the gas sensitive side is kept, as converted to the MgO basis, at from 2 wt % to 0.01 wt %.

* * * * *